(12) United States Patent
Bauer et al.

(10) Patent No.: US 7,459,576 B2
(45) Date of Patent: Dec. 2, 2008

(54) PROCESS FOR PREPARING AMINOALKYSILANES

(75) Inventors: Andreas Bauer, Simbach Am Inn (DE); Oliver Schäfer, Burghausen (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 11/908,179

(22) PCT Filed: Feb. 23, 2006

(86) PCT No.: PCT/EP2006/001652

§ 371 (c)(1), (2), (4) Date: Nov. 19, 2007

(87) PCT Pub. No.: WO2006/094643

PCT Pub. Date: Sep. 14, 2006

(65) Prior Publication Data

US 2008/0091041 A1 Apr. 17, 2008

(30) Foreign Application Priority Data

Mar. 10, 2005 (DE) .................. 10 2005 011 108

(51) Int. Cl.
*C07F 7/10* (2006.01)
(52) U.S. Cl. ..................................... 556/413
(58) Field of Classification Search ............... None
See application file for complete search history.

(56) References Cited

U.S. PATENT DOCUMENTS

2003/0130543 A1* 7/2003 Bauer et al. ............ 564/481

FOREIGN PATENT DOCUMENTS

DE        100 49 183  C1        1/2002

OTHER PUBLICATIONS

Speier, John L. et al., "Synthesis of (3-Aminoalkyl)silicon Compounds", Journal of Organic Chemistry, vol. 36, No. 21, 1971, pp. 3120-3126.

* cited by examiner

*Primary Examiner*—Samuel A Barts
(74) *Attorney, Agent, or Firm*—Brooks Kushman P.C.

(57) ABSTRACT

Useful products are recovered from the bottoms of aminoalkylsilane production in high yield and purity by reaction with alcohol, increasing the economics of aminoalkylsilane synthesis.

8 Claims, No Drawings

PROCESS FOR PREPARING AMINOALKYSILANES

CROSS-REFERENCE TO RELATED APPLICATION

This application is the U.S. national phase of PCT Appln. No. PCT/EP2006/001652 filed Feb. 23, 2006 which claims priority to German application DE 10 2005 011 108.4 filed Mar. 10, 2005.

BACKGROUND OF THE INVENTION

1. Field of the Invention

The invention relates to a process for preparing aminoalkylsilanes.

2. Description of the Related Art

Aminoalkylsilanes can, by way of example, be used as precursors for preparation of aminoalkyl-terminated polysiloxanes. They are also used as adhesion promoters.

DE 100 49 183 C1 and US 2003/0130543 A1 mention cyclic silazanes of the general formula (I) which are prepared via amination of chloroalkylsilanes

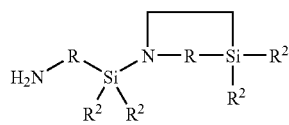

(I)

where
  R is a divalent Si—C— and Si—N-bonded, if appropriate cyano-or halogen-substituted, $C_3$-$C_{15}$-hydro-carbon radical in which one or more nonadjacent methylene units are optionally replaced by groups —O—, —CO—, —COO—, —OCO—, or —OCOO—, —S—, or —NR$^x$—, and in which one or more nonadjacent methyne units are optionally replaced by groups —N=, —N=N—, or —P=, where at least 3 and at most 6 atoms are present between the ring silicon and nitrogen atoms,
  R$^x$ is hydrogen or a $C_1$-$C_{10}$-hydrocarbon radical, if appropriate halogen-substituted, and
  R$^2$ is a hydrogen atom or a monovalent, if appropriate cyano- or halogen-substituted, Si—C—bonded $C_1$-$C_{20}$-hydrocarbon radical or $C_1$-$C_{20}$-oxyhydrocarbon radical, in which, in each case, one or more nonadjacent methylene units are optionally replaced by groups —O—, —CO—, —COO—, —OCO—, or —OCOO—, —S—, or —NR$^x$—, and in which one or more nonadjacent methyne units are optionally replaced by groups —N=, —N=N—, or —P=.

If the compounds of the general formula (I) are then hydrolyzed, the product is high yields of bisaminoalkyl-substituted disiloxanes of the general formula (II) practically free from byproduct:

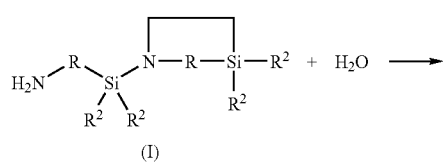

(I)

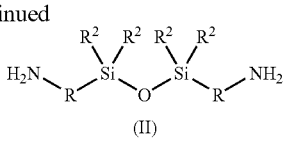

(II)

The particular advantage of the process described in DE 100 49 183 C1 and US 2003/0 130543 A1 is that highly reactive aminoalkylsilanes can be prepared cost-effectively from chloroalkylsilanes which have relatively good commercial availability.

However, a disadvantage of the process described in DE 10049 183 C1 and US 2003/0130543 A1 is that the reaction of the chioroalkylsilane precursor with ammonia does not give the desired product quantitatively, but instead gives secondary aminoalkylsilanes (IV) inter alia via a side reaction.

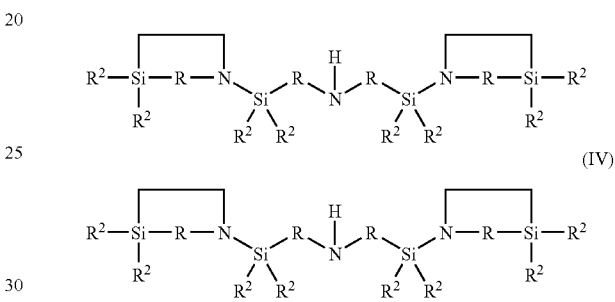

(IV)

These are then practically impossible to remove by distillation from the bottom product of distillation of the actual principal product, because their boiling point is extremely high, but they sometimes still comprise fractions which have the desired primary aminoalkyl function. It is moreover also technically difficult to achieve complete isolation of the target product of the general formula (I) present in the bottom product of distillation, as the bottom product becomes ever more viscous during the distillation process. Accordingly, a proportion (I) likewise remains in the bottom product of distillation. This product then has to be sent for expensive disposal.

SUMMARY OF THE INVENTION

The object of this invention was therefore to provide a process for work-up of a bottom product from crude silane distillation, permitting the primary and secondary aminoalkyl compounds remaining within that product to be obtained from the bottom product of distillation in a manner that permits commercialization. Surprisingly, these and other objects are achieved via the inventive process for preparing aminoalkylsilanes of the general formula (V) and/or (VI)

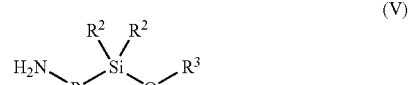

(V)

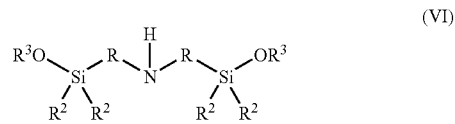

(VI)

wherein cyclic silazanes of the general formula (I) and/or (IV)

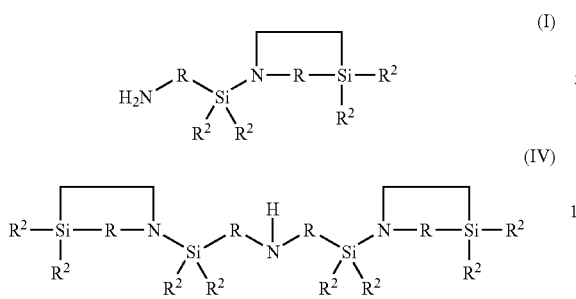

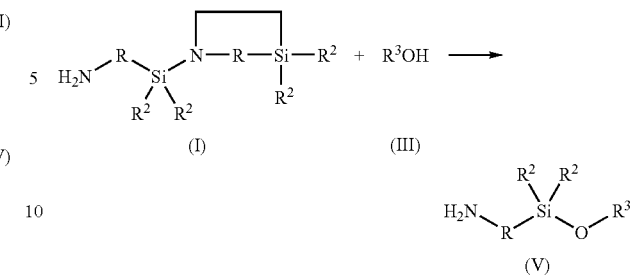

are reacted with alcohols of the general formula (III)

 (III), where

R is a divalent Si—C— and Si—N—bonded, if appropriate cyano- or halogen-substituted, $C_3$-$C_{15}$-hydrocarbon radical in which one or more nonadjacent methylene units are optionally replaced by groups —O—, —CO—, —COO—, —OCO—, or —OCOO—, —S—, or —$NR^x$—, and in which one or more nonadjacent methyne units can have been replaced by groups —N=, —N=N—, or —P=, where at least 3 and at most 6 atoms are located between the silicon atom and nitrogen atom of the ring, $R^x$ is hydrogen or a $C_1$-$C_{10}$-hydrocarbon radical, if appropriate halogen-substituted, and $R^2$ is a hydrogen atom or a monovalent, if appropriate cyano- or halogen-substituted, Si—C—bonded $C_1$-$C_{20}$-hydrocarbon radical or $C_1$-$C_{20}$-oxyhydrocarbon radical, in which, in each case, one or more nonadjacent methylene units can have been replaced by groups —O—, —CO—, —COO—, —OCO—, or —OCOO—, —S—, or —$NR^x$—, and in which one or more nonadjacent methyne units are optioally replaced by groups —N=, —N=N—, or —P=, and $R^3$ is a monovalent $C_1$-$C_{20}$-hydrocarbon radical in which, in each case one or more nonadjacent methylene units are replaced by groups —O—, —CO—, —COO—, —OCO—, or —OCOO—, —S—, or —$NR^x$—, and in which one or more nonadjacent methyne units are optionally replaced by groups —N=, —N=N—, or—P=.

The inventive process is preferably characterized in that the form in which the cyclic silazanes of the general formulae (I) and (IV) are used is that of the bottom product from distillation of a crude silane.

It is particularly preferable that the bottom product of distillation produced during distillation of a crude silane according to the processes of US 2003/0130543 A1 and DE 100 49 183 C1 is reacted with alcohols of the general formula (III)

 (III).

$R^3$ here is as defined above.

The bottom product of distillation described above retains content of the compound of the general formula (I), and this content is reacted with alcohols of the general formula (III). This produces aminoalkyl-substituted dialkylalkoxysilanes of the general formula (V).

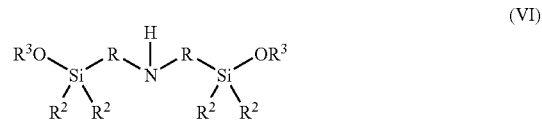

R, $R^2$, and $R^3$ here are as defined above.

Starting from the undesired byproducts of the general formula (IV), reaction with alcohols of the general formula (III) likewise produces aminoalkyl-substituted dialkylalkoxysilanes of the general formula (V), and also bis(dialkylalkoxysilylalkyl)amines of the general formula (VI).

(VI)

R, $R^2$, $R^3$ here are as defined above.

The process can either use stoichiometric amounts of alcohol (III), based on the molar amount of reactive Si N bonds in the compounds (I) and/or (IV), or else use nonstoichiometric amounts. If less than the stoichiometric amount of alcohol (III) is used in the process, the product is only partly alkoxylated. It is preferable to use an excess of alcohol (III) in the reaction. It is particularly preferable to use an excess of from 10 to 30 mol % of alcohol (III), based on the molar amount of reactive Si-N bonds in the compounds (I) and/or (IV).

Particular preference is given to a process for preparing aminoalkylsilanes in which R is a propylene radical.

Particular preference is likewise given to a process for preparing aminowlkylsilanes in which $R^2$ is a radical selected from the group consisting of methyl, ethyl, phenyl, vinyl, and trifluoropropyl.

Further particular preference is given to a process for preparing aminoalkylsilanes in which $R^3$ is a radical selected from the group consisting of methyl, ethyl, isopropyl, and methoxyethyl.

The reaction of the bottom product components with the alcohol proceeds exothermically in high yields, without byproducts. The compounds of the general formulae (V) and (VI) can then easily be isolated by distillation.

In order to ensure good mixing of the reaction components, the process is preferably carried out with stirring. Restrictions on the reaction temperature arise downward via the solubility of the reaction components and upward via the decomposition temperatures of the starting materials and products. The process is preferably carried out at a temperature of from 0°C. to 150° C. The process preferably takes place at a temperature above room temperature. A reaction temperature of at least 20°C., in particular at least 35° C., is particular preferred.

Isolation and purification of the compounds, of the general formulae (V) and (VI), then preferably follows, via fractionated distillation. The person skilled in the art is aware of possible modes of treatment of the compounds thus prepared.

The process can preferably be carried out in the presence or absence of further aprotic solvents. If aprotic solvents are used, preferred solvents or solvent mixtures have a boiling point or boiling range of up to 120° C. at 0.1 MPa. Examples of these solvents are ethers, such as dioxane, tetrahydrofuran, diethyl ether, diisopropyl ether, diethylene glycol dimethyl ether; chlorinated hydrocarbons, such as dichloromethane, trichloromethane, tetrachloromethane, 1,2-dichloroethane, trichloroethylene; hydrocarbons, such as pentane, n-hexane, hexane isomer mixtures, heptane, octane, cleaning solvent, petroleum ether, benzene, toluene, xylene; ketones, such as acetone, methyl ethyl ketone, diisopropyl ketone, methyl isobutyl ketone, known as MIBK; esters, such as ethyl acetate, butyl acetate, propyl propionate, ethyl butyrate, ethyl isobutyrate; carbon disulfide and nitrobenzene, or a mixture of these solvents.

The process is preferably carried out continuously or batchwise.

The advantages of the inventive process over the prior art are as follows. Firstly, the yield of the principal product is increased. Secondly, a byproduct is also isolated and is available for further use. Furthermore, disposal costs are significantly reduced, since most of the bottom product of distillation is worked up to give useful products. The cost-effectiveness of the entire process therefore increases considerably.

The definitions for all of the symbols mentioned above in the above formulae are mutually independent.

Unless otherwise stated, all of the quantitative and percentage data in the examples below are based on weight, all of the pressures are 0.10 MPa absolute, and all of the temperatures are 20° C.

EXAMPLES

Example 1

Methanolysis of a Cyclic Silazane to Give 3-aminopropyldimethylmethoxysilane 23 g (100 mmol) of N-((3-aminopropyl)dimethylsilyl)-2,2-dimethyl-1-aza-2-silacyclopentane were dissolved in 50 ml of THF and 30 ml of methanol were then added while cooling with ice. Distillation gave 28 g of aminopropyldimethylmethoxysilane (95% yield).

Example 2

Methanolysis of a Bottom Product of Distillation using 10% Excess of Alcohol 1613.5 g of the bottom product of distillation described above were used as initial charge in a 4 l three-necked flask inertized with argon. This corresponded to a theoretical amount of 7.0 mol of N-((3-aminopropyl)dimethylsilyl)-2,2-dimethyl-1-aza-2-silacyclopentane. 493.4 g (15.4 mol) of methanol were then added dropwise with stirring within a period of 2 h, in such a way as to prevent the temperature of the reaction mixture from exceeding 40° C. Stirring of the mixture was then continued for about 1 hour at room temperature.

Constitution of reaction mixture (GC, in % by area):

| 3.2% | of methanol |
| 38.2% | of (V) |
| 51.4% | of (VI) |

Fractionated distillation gave 732.7 g of (V) and 930.4 g of (VI), in each case with GC purity>96%.

Example 3

Methanolysis of a Bottom Product of Distillation using 80% Excess of Alcohol 1500.0 g of the bottom product of distillation by analogy with Example 2 were used as initial charge in a 4 l three-necked flask inertized with argon. This corresponded to a theoretical amount of 6.5 mol of N-((3-aminopropyl)dimethylsilyl)-2,2-dimethyl-1-aza-2-silacyclopentane. 750.0 g (23.4 mol) of methanol were then added dropwise with stirring within a period of 2 h, in such a way as to prevent the temperature of the reaction mixture from exceeding 40° C. Stirring of the mixture was then continued for 1 hour at room temperature.

Constitution of reaction mixture (GC, in % by area):

| 20.3% | of methanol |
| 31.1% | of (V) |
| 43.1% | of (VI) |

Fractionated distillation gave 662.7 g of (V) and 787.8 g of (VI), in each case with GC purity>96%.

What is claimed is:

1. A process for preparing aminoalkylsilanes of the general formula (V) and/or (VI),

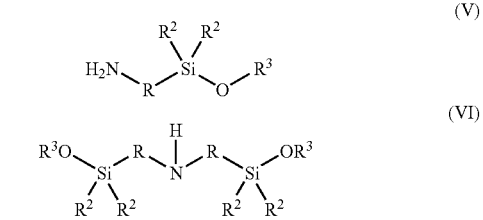

comprising reacting cyclic silazanes of the formula (I), (IV), or both (I) and (IV)

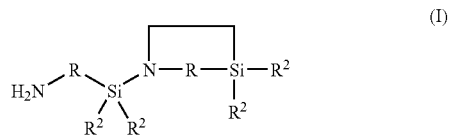

with alcohols of the formula (III)

$$R^3\text{—OH} \qquad (III),$$

where

R is a divalent, optionally cyano- or halogen-substituted $C_3$-$C_{15}$-hydrocarbon radical in which one or more non-adjacent methylene units are optionally replaced by groups —O—, —CO—, —COO—, —OCO—, or —OCOO—, —S—, or —NR$^x$—, and in which one or more nonadjacent methyne units are optionally replaced by groups —N=, —N=, or —P=, R being bonded to silicon by an Si—C bond and to nitrogen by a C—N bond, where at least 3 and at most 6 atoms are located between silicon and nitrogen atoms in the ring structure

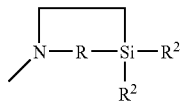

of cyclic silazenes(I and IV),

R$^x$ is hydrogen or a C$_1$-C$_{10}$-hydrocarbon radical, optionally halogen-substituted, and R$^2$ is a hydrogen atom or a monovalent, optionally cyano- or halogen-substituted, Si—C— bonded C$_1$-C$_{20}$-hydrocarbon radical or C$_1$-C$_{20}$-oxyhydrocarbon radical, in which, in each case, one or more nonadjacent methylene units are optionally replaced by groups —O—, —CO—, —COO—, —OCO—, or —OCOO—, —S—, or—NR$^x$—, and in which one or more nonadjacent methyne units are optionally replaced by groups —N=, —N=, or —P=, and R$^3$ is a monovalent C$_1$-C$_{20}$-hydrocarbon radical in which in each case one or more nonadjacent methylene units are optionally replaced by groups —O—, —CO—, —COO—, —OCO—, or —OCOO—, —S—, or —NR$^x$—, and in which one or more nonadjacent methyne units are optionally replaced by groups —N=, —N=N—, or —P=.

2. The process of claim 1, wherein the cyclic silazanes of the formulae (I) and (IV) comprise a bottom product from distillation of a crude silane.

3. The process of claim 1, wherein R is a propylene radical.

4. The process of claim 1, wherein R$^2$ is a radical selected from the group consisting of methyl, ethyl, phenyl, vinyl, and trifluoropropyl.

5. The process of claim 1, wherein R$^3$ is a radical selected from the group consisting of methyl, ethyl, isopropyl, and methoxyethyl.

6. The process of claim 1, wherein the process is carried out at a temperature of from 0° C. to 150° C.

7. The process of claim 1, wherein the process is carried out with stirring.

8. The process of claim 1, wherein following said step of reacting, compounds of the formulae (V) and (VI) are isolated and purified by fractional distillation.

* * * * *

UNITED STATES PATENT AND TRADEMARK OFFICE
CERTIFICATE OF CORRECTION

PATENT NO. : 7,459,576 B2 Page 1 of 1
APPLICATION NO. : 11/908179
DATED : December 2, 2008
INVENTOR(S) : Andreas Bauer et al.

It is certified that error appears in the above-identified patent and that said Letters Patent is hereby corrected as shown below:

Column 7, Line 3, Claim 1:

Delete "-N= --"

and insert:

--N= N--

Column 7, Line 25, Claim 1:

Delete "-N= --"

and insert:

--N= N--

Column 8, Line 22, Claim 8:

Delete ",".

Signed and Sealed this

Fourteenth Day of April, 2009

JOHN DOLL
*Acting Director of the United States Patent and Trademark Office*